US009044753B2

(12) United States Patent
Atwood et al.

(10) Patent No.: US 9,044,753 B2
(45) Date of Patent: Jun. 2, 2015

(54) THERMAL CYCLER FOR PCR

(75) Inventors: John G. Atwood, West Redding, CT (US); Adrian Fawcett, Pleasanton, CA (US); Keith S. Ferrara, Stratford, CT (US); Paul M. Hetherington, Golden Bridge, NY (US); Richard W. Noreiks, Stratford, CT (US); Douglas E. Olsen, New Fairfield, CT (US); John R. Widomski, Shelton, CT (US); Charles M. Wittmer, Trumbull, CT (US)

(73) Assignee: Applied Biosystems, LLC, Carlsbad, CA (US)

( * ) Notice: Subject to any disclaimer, the term of this patent is extended or adjusted under 35 U.S.C. 154(b) by 999 days.

(21) Appl. No.: 11/654,239

(22) Filed: Jan. 17, 2007

(65) Prior Publication Data

US 2007/0113880 A1   May 24, 2007

Related U.S. Application Data

(60) Continuation of application No. 11/057,960, filed on Feb. 15, 2005, now Pat. No. 7,537,377, which is a (Continued)

(51) Int. Cl.
*H01L 35/28* (2006.01)
*B01L 7/00* (2006.01)
(Continued)

(52) U.S. Cl.
CPC .......... *B01L 7/52* (2013.01); *B01L 2300/0829* (2013.01); *B01L 2300/1822* (2013.01);
(Continued)

(58) Field of Classification Search
CPC .............. B01L 7/52; B01L 2300/0829; B01L 2300/1822; B01L 2300/1827; C12Q 1/686; H01L 35/30; F25B 21/04; G01R 27/205; G05D 23/1919
USPC ....................................... 435/303.1; 136/203
See application file for complete search history.

(56) References Cited

U.S. PATENT DOCUMENTS 2,146,464 A   2/1939  Briddell
2,188,163 A   1/1940  Sherman (Continued)

FOREIGN PATENT DOCUMENTS

DE   4037 955 A1   6/1991
DE   4037955 A1    6/1991

(Continued)

OTHER PUBLICATIONS

Two European Search Reports, both mailed Oct. 28, 1998, for European Application Application No. EP 03 022 674.4-2113(4 pages + 9 pages).

(Continued)

*Primary Examiner* — William H Beisner
*Assistant Examiner* — Danielle Henkel

(57) ABSTRACT

An instrument for performing highly accurate PCR employing an assembly, a heated cover and an internal computer. The assembly is made up of a sample block, a number of Peltier thermal electric devices and heat sink, clamped together. The sample block temperature is changed exclusively by the thermoelectric devices controlled by the computer. The sample block is of low thermal mass and is constructed of silver. The Peltier devices are designed to provide fast temperature excursions over a wide range. The heat sink has a perimeter trench to minimize edge losses and is adjacent to a continuously variable fan. A perimeter heater is used to improve the thermal uniformity across the sample block to approximately ±0.2° C. A heated platen pushes down onto the tube caps to apply a minimum acceptable force for seating the tubes into the block, ensuring good thermal contact with the block. The force is applied about the periphery of the tube caps to prevent distortion of the caps during thermal cycling. The platen is heated to provided thermal isolation from ambient conditions and to prevent evaporation from the surface of the sample into the upper portion of the sample tube. A control algorithm manipulates the current supplied to the thermoelectric coolers such that the dynamic thermal performance of the block can be controlled so that pre-defined thermal profiles for the sample temperature can be executed. The sample temperature is calculated instead of measured using a design specific model and equations. The control software includes calibration diagnostics which permit variation in the performance of thermoelectric coolers from instrument to instrument to be compensated for such that all instruments perform identically. The block/heat sink assembly can be changed to another of the same or different design. The assembly carries the necessary information required to characterize its own performance in an on-board memory device, allowing the assembly to be interchangeable among instruments while retaining its precision operating characteristics. The instrument has a graphical user interface. The instrument monitors the thermoelectric devices and warns of changes in resistance that may result in failure.

24 Claims, 13 Drawing Sheets

Related U.S. Application Data division of application No. 09/075,392, filed on May 8, 1998, now Pat. No. 7,133,726, which is a continuation of application No. PCT/US98/06189, filed on Mar. 30, 1998.

(60) Provisional application No. 60/046,122, filed on May 9, 1997, provisional application No. 60/041,754, filed on Mar. 28, 1997.

(51) Int. Cl.
*C12Q 1/68* (2006.01)
*F25B 21/04* (2006.01)
*G01R 27/20* (2006.01)
*G05D 23/19* (2006.01)
*H01L 35/30* (2006.01)

(52) U.S. Cl.
CPC ......... *B01L2300/1827* (2013.01); *C12Q 1/686* (2013.01); *F25B 21/04* (2013.01); *F25B 2321/021* (2013.01); *G01R 27/205* (2013.01); *G05D 23/1919* (2013.01); *H01L 35/30* (2013.01)

(56) References Cited

U.S. PATENT DOCUMENTS

| | | | |
|---|---|---|---|
| 3,075,377 A | 1/1963 | Lang | |
| 3,182,391 A | 5/1965 | Charland et al. | |
| 3,210,216 A | 10/1965 | William | |
| 3,552,185 A | 1/1971 | Goode et al. | |
| 3,733,887 A | 5/1973 | Stanley et al. | |
| 3,766,360 A * | 10/1973 | Eddleman et al. | 219/415 |
| 3,821,058 A | 6/1974 | Miller | |
| 3,842,346 A | 10/1974 | Bobbitt | |
| 3,998,592 A | 12/1976 | Pyle | |
| 4,149,025 A | 4/1979 | Niculescu | |
| 4,456,581 A | 6/1984 | Edelmann et al. | |
| 4,498,896 A | 2/1985 | Leis | |
| 4,530,608 A | 7/1985 | O'Neill | |
| 4,632,908 A | 12/1986 | Schultz | |
| 4,639,883 A | 1/1987 | Michaelis | |
| 4,676,951 A | 6/1987 | Armes | |
| 4,782,644 A | 11/1988 | Haarer et al. | |
| 4,782,664 A | 11/1988 | Sterna et al. | |
| 4,856,986 A | 8/1989 | Macocco et al. | |
| 4,865,986 A | 9/1989 | Coy et al. | |
| 4,881,038 A | 11/1989 | Champlin | |
| 4,967,382 A | 10/1990 | Hall | |
| 5,038,852 A | 8/1991 | Johnson et al. | |
| 5,040,381 A | 8/1991 | Hazen | |
| 5,061,630 A * | 10/1991 | Knopf et al. | 422/500 |
| 5,080,495 A | 1/1992 | Hashimoto et al. | |
| 5,224,778 A | 7/1993 | Grossman et al. | |
| 5,232,667 A | 8/1993 | Hieb et al. | |
| 5,237,821 A | 8/1993 | Okumura et al. | |
| 5,248,934 A | 9/1993 | Roveti | |
| 5,282,543 A | 2/1994 | Picozza et al. | |
| 5,318,361 A | 6/1994 | Chase et al. | |
| 5,333,675 A | 8/1994 | Mullis et al. | |
| 5,385,022 A | 1/1995 | Kornblit | |
| 5,410,130 A | 4/1995 | Braunstein | |
| 5,411,599 A | 5/1995 | Horn et al. | |
| 5,412,171 A | 5/1995 | Yahav et al. | |
| 5,431,021 A | 7/1995 | Gwilliam et al. | |
| 5,441,576 A | 8/1995 | Bierschenk et al. | |
| 5,475,610 A * | 12/1995 | Atwood et al. | 700/269 |
| 5,495,093 A | 2/1996 | Griffith | |
| 5,525,300 A | 6/1996 | Danssaert et al. | |
| 5,527,510 A | 6/1996 | Atwood et al. | |
| 5,568,977 A | 10/1996 | Gschwind et al. | |
| 5,600,575 A | 2/1997 | Anticole | |
| 5,602,756 A | 2/1997 | Atwood | |
| 5,616,301 A | 4/1997 | Moser et al. | |
| 5,635,409 A | 6/1997 | Moslehi | |
| 5,656,493 A | 8/1997 | Mullis et al. | |
| 5,679,457 A | 10/1997 | Bergerson | |
| 5,711,604 A | 1/1998 | Nakamura | |
| 5,720,406 A * | 2/1998 | Fassbind et al. | 220/23.4 |
| 5,736,333 A | 4/1998 | Livak et al. | |
| 5,743,643 A | 4/1998 | Gronet et al. | |
| 5,744,975 A | 4/1998 | Notohardjono et al. | |
| 5,756,878 A | 5/1998 | Muto et al. | |
| 5,779,981 A | 7/1998 | Danssaert et al. | |
| 5,795,547 A | 8/1998 | Moser et al. | |
| 5,827,480 A | 10/1998 | Haff et al. | |
| 5,834,828 A | 11/1998 | Horn et al. | |
| 5,841,064 A | 11/1998 | Maekawa et al. | |
| 5,849,208 A | 12/1998 | Hayes et al. | |
| 5,882,903 A | 3/1999 | Andrevski et al. | |
| 5,914,065 A | 6/1999 | Alavi | |
| 5,928,907 A | 7/1999 | Woudenberg et al. | |
| 5,973,299 A | 10/1999 | Reader | |
| 5,985,651 A * | 11/1999 | Hunicke-Smith | 435/285.1 |
| 6,015,534 A | 1/2000 | Atwood | |
| 6,019,505 A | 2/2000 | Bonne et al. | |
| 6,046,442 A | 4/2000 | Kawamura et al. | |
| 6,054,263 A | 4/2000 | Danssaert et al. | |
| 6,153,012 A | 11/2000 | Rupp et al. | |
| 6,331,075 B1 | 12/2001 | Amer et al. | |
| 6,348,176 B1 | 2/2002 | Hammer et al. | |
| 6,482,638 B1 | 11/2002 | Patil et al. | |
| 6,635,492 B2 | 10/2003 | Gunter | |
| 6,713,297 B2 | 3/2004 | McMillan et al. | |
| 6,717,118 B2 | 4/2004 | Pilavdzic et al. | |
| 6,734,401 B2 | 5/2004 | Bedingham et al. | |
| 6,787,338 B2 | 9/2004 | Wittwer et al. | |
| 6,818,437 B1 | 11/2004 | Gambini et al. | |
| 6,859,050 B2 | 2/2005 | Van et al. | |
| 6,889,468 B2 | 5/2005 | Bedingham et al. | |
| 6,962,821 B2 | 11/2005 | Danssaert et al. | |
| 7,008,789 B2 | 3/2006 | Gambini et al. | |
| 7,051,536 B1 | 5/2006 | Cohen et al. | |
| 7,133,726 B1 | 11/2006 | Atwood et al. | |
| 7,504,241 B2 | 3/2009 | Atwood et al. | |
| 7,537,377 B2 * | 5/2009 | Atwood et al. | 374/1 |
| 7,645,070 B2 | 1/2010 | Atwood et al. | |
| 2002/0047003 A1 | 4/2002 | Bedingham et al. | |
| 2002/0106314 A1 | 8/2002 | Pelrine et al. | |
| 2002/0191826 A1 | 12/2002 | Benett et al. | |
| 2003/0036189 A1 | 2/2003 | Benett et al. | |
| 2003/0066830 A1 | 4/2003 | Reed et al. | |
| 2003/0152492 A1 | 8/2003 | Chang et al. | |
| 2003/0169799 A1 | 9/2003 | Cho et al. | |
| 2003/0214994 A1 | 11/2003 | Schicke et al. | |
| 2004/0001780 A1 | 1/2004 | Schirr et al. | |
| 2004/0014202 A1 | 1/2004 | King et al. | |
| 2004/0038390 A1 | 2/2004 | Boege et al. | |
| 2005/0145273 A1 | 7/2005 | Atwood et al. | |
| 2007/0014695 A1 | 1/2007 | Yue et al. | |
| 2007/0289314 A1 | 12/2007 | Liebmann et al. | |
| 2008/0124723 A1 | 5/2008 | Dale et al. | |
| 2008/0314431 A1 | 12/2008 | Atwood et al. | |
| 2009/0275014 A1 | 11/2009 | Maltezos et al. | |
| 2010/0120099 A1 | 5/2010 | Heimberg et al. | |
| 2010/0124766 A1 | 5/2010 | Ng et al. | |
| 2010/0173400 A1 | 7/2010 | Atwood et al. | |
| 2010/0233763 A1 | 9/2010 | Shigeura et al. | |
| 2011/0136219 A1 | 6/2011 | Shin et al. | |
| 2012/0021424 A1 | 1/2012 | Sandell | |

FOREIGN PATENT DOCUMENTS

| | | |
|---|---|---|
| EP | 0 236 069 A2 | 9/1987 |
| EP | 0236069 A2 | 9/1987 |
| EP | 0 342 155 A2 | 11/1989 |
| EP | 0342155 A2 | 11/1989 |
| EP | 0 362 173 A1 | 4/1990 |
| EP | 0362173 B1 | 4/1990 |
| EP | 0 488 769 A2 | 6/1992 |
| EP | 0488769 A2 | 6/1992 |
| EP | 0 640 828 A1 | 3/1995 |
| EP | 0 642 828 A1 | 3/1995 |

(56) References Cited

FOREIGN PATENT DOCUMENTS

| EP | 0 642 828 B1 | 3/1995 |
|---|---|---|
| EP | 0 642 831 A1 | 3/1995 |
| EP | 0640828 A1 | 3/1995 |
| EP | 0642828 A1 | 3/1995 |
| EP | 0642831 A1 | 3/1995 |
| EP | 1 510 823 A3 | 6/2005 |
| EP | 1510823 A2 | 7/2005 |
| JP | 5-060708 A | 3/1993 |
| JP | 6-233670 A | 8/1994 |
| JP | 7-151764 A | 6/1995 |
| JP | 7-163397 A | 6/1995 |
| JP | 7-167865 A | 7/1995 |
| WO | 93/09486 A1 | 5/1993 |
| WO | 9309486 | 5/1993 |
| WO | WO 93/09486 | 5/1993 |
| WO | 95/27196 A1 | 10/1995 |
| WO | WO 95/27196 | 10/1995 |
| WO | 97/21089 A1 | 6/1997 |
| WO | WO 97/21089 | 6/1997 |
| WO | 98/43740 A3 | 10/1998 |

OTHER PUBLICATIONS

Paul D. Levine, et al. "Precision AC Measurements of Temperature Below 90 K," IEEE Transactions on Instrumentation and Measurement, Apr. 1989.

Extended European Search Report for European application No. 09013036.0, date mailed Feb. 1, 2010.

Extended European Search Report for European application No. 09016131.6, date mailed Apr. 7, 2010.

PCT/US1998/006189, "International Search Report", mailed Oct. 28, 1998, 9 pages.

\* cited by examiner

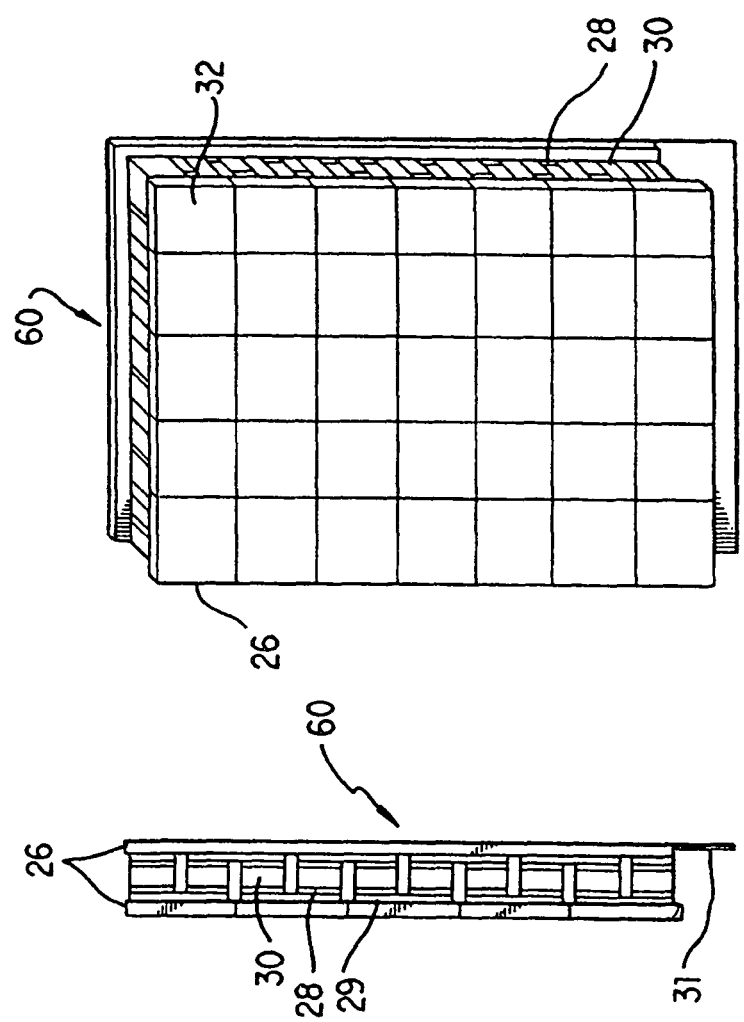

THERMAL CYCLER FOR PCR

RELATED APPLICATIONS

This application is a continuation application of U.S. patent application Ser. No. 11/057,960, filed Feb. 15, 2005, which in turn is a divisional application of U.S. patent application Ser. No. 09/075,392, filed May 8, 1998, (U.S. Pat. No. 7,133,726), which is a continuation of PCT/US98/06189, filed Mar. 30, 1998, which claims benefit of U.S. Provisional Application No. 60/046,122, filed May 9, 1997, and claims benefit of U.S. Provisional Application No. 60/041,754, filed Mar. 28, 1997.

FIELD OF THE INVENTION

This invention pertains to the field of computer controlled instruments for performing the Polymerase Chain Reaction (PCR). More particularly, the invention pertains to automated instruments that perform the reaction simultaneously on many samples and produce very precise results by using thermal cycling.

BACKGROUND OF THE INVENTION

The background of the invention is substantially as stated in U.S. Pat. No. 5,475,610 which is herein incorporated by reference.

To amplify DNA (Deoxyribose Nucliec Acid) using the PCR process, it is necessary to cycle a specially constituted liquid reaction mixture through several different temperature incubation periods. The reaction mixture is comprised of various components including the DNA to be amplified and at least two primers sufficiently complementary to the sample DNA to be able to create extension products of the DNA being amplified. A key to PCR is the concept of thermal cycling: alternating steps of melting DNA, annealing short primers to the resulting single strands, and extending those primers to make new copies of double-stranded DNA. In thermal cycling die PCR reaction mixture is repeatedly cycled from high temperatures of around 90° C. for melting the DNA, to lower temperatures of approximately 40° C. to 70° C. for primer annealing and extension. Generally, it is desirable to change the sample temperature to the next temperature in the cycle as rapidly as possible. The chemical reaction has an optimum temperature for each of its stages. Thus, less time spent at non optimum temperature means a better chemical result is achieved. Also a minimum time for holding the reaction mixture at each incubation temperature is required after each said incubation temperature is reached. These minimum incubation times establish the minimum time it takes to complete a cycle. Any tune in transition between sample incubation temperatures is time added to this minimum cycle time. Since the number of cycles is fairly large, this additional time unnecessarily heightens the total time needed to complete the amplification.

In some previous automated PCR instruments, sample tubes are inserted into sample wells on a metal block. To perform the PCR process, the temperature of the metal block is cycled according to prescribed temperatures and times specified by the user in a PCR protocol file. The cycling is controlled by a computer and associated electronics. As the metal block changes temperature, the samples in the various tubes experience similar changes in temperature. However, in these previous instruments differences in sample temperature are generated by non-uniformity of temperature from place to place within the sample metal block. Temperature gradients exist within the material of the block, causing some samples to have different temperatures than others at particular times in the cycle. Further, there arc delays in transferring heat from the sample block to the sample, and those delays differ across the sample block. These differences in temperature and delays in heat transfer cause the yield of the PCR process to differ from sample vial to sample vial. To perform the PCR process successfully and efficiently, and to enable so-called quantitative PCR, these time delays and temperature errors must be minimized to the greatest extent possible. The problems of minimizing non-uniformity in temperature at various points on the sample block, and time required for and delays in heat transfer to and from the sample become particularly acute when the size of the region containing samples becomes large as in the standard 8 by 12 microtiter plate.

Another problem with current automated PCR instruments is accurately predicting the actual temperature of the reaction mixture during temperature cycling. Because the chemical reaction of tie mixture has an optimum temperature for each of its stages, achieving that actual temperature is critical for good analytical results. Actual measurement of the temperature of the mixture in each vial is impractical because of the small volume of each vial and the large number of vials.

SUMMARY OF THE INVENTION

According to the invention, there is provided an apparatus for performing the polymerase Chain Reaction comprising an assembly capable of cycling samples through a series of temperature excursions, a heated cover and a computer to control the process.

The invention further encompasses a sample block with low thermal mass for rapid temperature excursions. The sample block is preferably manufactured from silver for uniform overall heat distribution and has a bottom plate for uniform lateral heat distribution. In addition, to further offset heat losses and resulting temperature gradients from the center to the edges, a center pin is used as a conducting path to a heat sink.

The invention also provides a method and apparatus for achieving rapid heating and cooling using Peltier thermoelectric devices. These devices are precisely matched to each other. They are constructed using die cut alumina on one side to minimize thermal expansion and contraction. The devices are constructed of bismuth telluride using specific dimensions to achieve matched heating and cooling rates. They are designed using minimal copper thicknesses and minimal ceramic thicknesses to further reduce their heat load characteristics and are assembled using a specific high temperature solder in specified quantities.

The invention is also directed to a heatsink constructed with a perimeter trench to limit heat conduction and losses from its edges. Furthermore, the heatsink has an associated variable speed fan to assist in both maintaining a constant temperature and in cooling.

The invention is also directed to a clamping mechanism to hold the sample block to the heat sink with the thermoelectric devices positioned in between. The mechanism is designed to provide evenly distributed pressure with a minimal heat load. The design allows the use of thermal grease as an interface between the sample block, and the thermoelectric devices and between the thermoelectric devices and the heatsink.

There is also provided a perimeter heater to minimize the thermal non-uniformity across the sample block. The perimeter heater is positioned around the sample block to counter the heat loss from the edges. Power is applied to the heater in proportion to the sample block temperature with more power applied when the sample block is at higher temperatures and less power applied when the sample block is at lower temperatures.

There is also provided a heated cover, designed to keep the sample tubes closed during cycling and to heat the upper portion of the tubes to prevent condensation. The heated cover applies pressure on the sample tube cap perimeter to avoid distorting the cap's optical qualities. The cover is self-aligning, using a skirt which mates with a sample tube tray.

The invention is also directed to a method and apparatus for determining an ideal temperature ramp rate which is determined so as to take advantage of sample block temperature overshoots and undershoots in order to minimize cycle time.

The invention also includes a method and apparatus for characterizing the thermal power output from the thermoelectric cooling devices to achieve linear temperature control and linear and non-linear temperature ramps.

The invention is further directed to a method for predicting the actual temperature of the reaction mixture in the sample vials at any given time during the PCR protocol.

The invention also includes a method and apparatus for utilizing calibration diagnostics which compensate for variations in the performance of the thermoelectric devices so that all instruments perform identically. The thermal characteristics and performance of the assembly, comprised of the sample block, thermoelectric devices and heatsink, is stored in an on-board memory device, allowing the assembly to be moved to another instrument and behave the same way.

The invention further includes a method and apparatus for measuring the AC resistance of the thermoelectric devices to provide early indications of device failures.

BRIEF DESCRIPTION OF THE DRAWINGS

FIG. 2 is an enlarged, isometric view of a thermoelectric device constructed according to the invention.

FIG. 2A is a side, elevational view of a thermoelectric device constructed according to the invention.

DETAILED DESCRIPTION OF THE INVENTION

Figure 1:
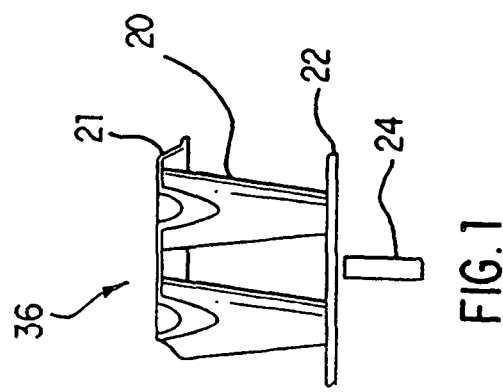
FIG. 1 is a cross sectional view of a portion of the sample block according to the invention.

Generally, in the case of PCR, it is desirable to change the sample temperature between the required temperatures in the cycle as quickly as possible for several reasons. First the chemical reaction has an optimum temperature for each of its stages and as such less time spent at non-optimum temperatures means a better chemical result is achieved. Secondly a minimum time is usually required at any given set point which sets a minimum cycle time for each protocol and any time spent in transition between set points adds to this minimum time. Since the number of cycles is usually quite large, this transition time can significantly add to the total time needed to complete the amplification.

The absolute temperature that each reaction tube attains during each step of the protocol is critical to the yield of product. As the products arc frequently subjected to qutanitation, the product yield from tube to tube must be as uniform as possible and therefore both the steady-state and dynamic thermal uniformity must be excellent across the block.

Heat-pumping into and out of the samples is accomplished by using Peltier thermoelectric devices. These are constructed of pellets of n-type and p-type bismuth telluride connected alternately in series. The interconnections between the pellets is made with copper which is bonded to a substrate, usually a ceramic (typically alumina).

The amount of heat-pumping required is dependent on the thermal load and the ramp rate, that is, the rate at which the temperature is required to change. The sample tube geometry and sample volumes are not variables as the sample tubes arc established as an industry standard, fitting into many other types of instruments such as centrifuges. The sample volume is defined by user need. Therefore the design variables primarily affect the sample block, thermoelectric devices, heatsink, fan and the thermal interface media between the thermoelectric devices and both the heatsink and the sample block.

The block geometry must also meet the necessary thermal uniformity requirements because it is the primary contributor to lateral conduction and therefore evens out any variation in thermal uniformity of the thermoelectric coolers themselves. The conflicting requirements of rapid ramp rates (indicating low thermal mass) and high lateral conduction (indicating a large material mass) are met by concentrating the bulk of the block structure in a base plate, and minimizing the thermal mass of the upper portion of the block which holds the sample tubes. The optimal material for block fabrication is pure silver which has relatively low thermal mass and very good thermal conduction. Silver also lends itself well to electroforming. In practice the optimal block geometry has a light electroformed upper portion to hold (he sample tubes fixed to a relatively thick base plate which provides lateral conduction. The thermal mass of the block is concentrated in the base plate where the material contributes the most to thermal uniformity. The electroformed portion of the block has a minimum thickness which is defined by two parameters: first, the material cannot be so thin as to make it too delicate for normal handling; second, the wall thickness is required to conduct heat out of the upper regions of the sample tube. Circulation in the sample itself is achieved by convection inside the tube and sample temperature is relatively uniform along the height of the tube, but good thermal conductivity between the tube walls and the base plate increases the effective surface area available for conduction of heat between the sample and the base plate. The base plate thickness has a minimum value defined by lateral conduction requirements which is a function of the thermal uniformity of the thermoelectric coolers and structural rigidity.

Another contributor to the thermal mass is the alumina ceramic layers which form part of the structure of the thermoelectric cooler itself. There are two alumina layers in the construction of the thermoelectric cooler, one on the sample block side and another on the heatsink side. The thickness of die layers should be minimized as much as possible, in this case the practical limit of thinness for the alumina thickness is defined by the manufacturing requirements of thermoelectric cooler fabrication. This particular layer or ceramic could ill principal be replaced by a different layer altogether such as a thin sheet of Kapton which would reduce the thermal mass even more, but at the present time although coolers are available with this structure, reliability is unproven. It is anticipated that once the technology has been developed further, then a cooler of such a design may be preferred. However, the thin alumina layers also contribute to system reliability.

The copper conductors within the cooler are a significant thermal load and are not overlooked in the design of the system. The thickness of the copper traces is defined by the requirement of carrying current through the device. Once the current is known the required copper thickness can be calculated.

Sample Block

FIG. 1 shows a cross sectional view of a portion of the sample block 36 which typically has 96 wells 20, each for receiving a sample vial. The sample block is constructed of silver and comprises an upper support plate 21 and the sample wells 20 electroformed as one piece fastened to a base plate 22. The base plate 22 provides lateral conduction to compensate for any difference in the thermal power output across the surface of each individual thermoelectric device and for differences from one thermoelectric device to another.

There are always boundary losses in any thermal system. In a rectangular configuration there is more heat loss in the corners. One solution is to use a round sample block, but the microtiter tray format that is in common usage is rectangular and this must be used to retain compatibility with other existing equipment. Once the edge effects have been eliminated using all standard means, such as insulation etc., there remains a tendency for the center of the sample block to be warmer than the corners. Typically it is this temperature difference that defines the thermal uniformity of the sample block. In accordance with the invention, the center temperature is reduced by providing a small thermal connection from the center of the sample block to the heat sink. By using a pin 24 which acts as a "heat leak" in the center of the sample block, the temperature gradient across the sample block can be reduced to an acceptable level. The amount of conduction required is quite small and a 1.5 mm diameter stainless steel pin has been found to be sufficient. Moreover, a pin made of the polymer ULTEM, manufactured by General Electric may also be used. As more fully described below, the pin also serves to help position and lock into place components of the assembly illustrated in FIG. 4.

Peltier Thermoelectric Devices (TEDs)

Thermal uniformity of the sample block is critical to PCR performance. One of the most significant factors affecting the uniformity is variations in the thermoelectric device performance between devices. The most difficult point at which to achieve good uniformity is during a constant temperature cycle far from ambient In practice this is a constant temperature cycle at approximately 95° C. The thermoelectric devices are matched under these conditions to make a set of devices for each heatsink assembly which individually produce the same temperature for a given input current. The thermoelectric devices are matched to within 0.2° C. in any given set, this value being derived from the maximum discrepancy that can be rectified by the lateral conduction of the sample block baseplate.

FIG. 2A shows a side view of a typical Peltier thermal electric device 60. The device is composed of bismuth telluride pellets 30, sandwiched between two alumna layers 26. The pellets arc electrically connected by solder joints 28 to copper traces 29 plated onto the alumina layers. One alumina layer has an extension 31 to facilitate electrical connections. The thickness of the extended areas is reduced to decrease the thermal load of the device.

FIG. 2 shows an isometric view of a typical Peltier thermoelectric device. The alumina layer 26 that forms the outer wall of the thermoelectric device, expands and contracts during temperature cycling at a different rate than the sample block 19. The motion of the alumina is transmitted directly to the solder 28 connecting the internal bismuth telluride pellets 30. This motion can be reduced dramatically by cutting the alumina into small pieces 32 called die so that the field of expansion is small. The minimum size of the die is defined by the size of the copper traces required to carry current through the thermoelectric device and the requirements that the device retain some strength for handling.

Using thin alumina layers in the thermal electric device (of the order of 0.508 mm) not only reduces the thermal load but also means that for a given required heat pumping rate the temperature that the ends of the pellet reaches is reduced due to the increase in thermal conductivity k. This enhances reliability by reducing the thermal stress on the solder joint.

Generally in PCR the reaction temperatures are above ambient and in the range 35 to 96° C. In the most important cases the block is heated or cooled between two above ambient temperatures where the flow of heat due to conduction is from the block to the heat sink. The key to optimizing the system cycle time, given an optimized block configuration, is to balance the boost to the ramp rate when cooling provided by the conduction, against the boost provided to the heating ramp rate by the Joule effect of resistance heating.

If the cross-section of the bismuth telluride pellets in a given thermoelectric device were considered constant, the heating ramp rate would be increased by increasing the height of the pellet. This is because the conduction path through the thermoelectric device would be made longer thereby decreasing k. This also has the effect of reducing the current required to maintain a given block temperature in the steady state. During the down ramp, i.e. cooling the block, the decreased k means that the conduction contribution will be reduced and so the down ramp rate will be reduced.

Conversely, if the height of the bismuth telluride pellet were to be decreased for a given cross-section, then k would be increased. This would increase the current required to maintain an elevated temperature in the steady state and would increase the cooling ramp rate. Heating ramp rates would be reduced as a larger portion of the heat in the block would be conducted directly to the heat sink. Decreasing the bismuth telluride pellet height also increases the holding power required for a given temperature due to the losses through the thermoelectric devices and reduces the thermal load, increasing the maximum possible ramp rate for given power. Therefore the optimized thermoelectric device can be derived by adjusting the height of the Bismuth Telluride pellets until the heating rate matches the cooling rate.

The ratio 1: A for the pellets also defines the resistance of the device i.e.

$$R = nr(h/A)$$

where n is the number of pellets, r is the resistivity of the Bismuth Telluride being used, h is the height of the pellet and A is the cross-sectional area.

The resistance must be measured as an AC resistance because of the Seebeck effect. Because the geometry defines the resistance of the device, another design boundary is encountered in that the device must use a cost effective current to voltage ratio because too high a current requirement pushes up the cost of the amplifier. The balanced solution for the silver electroformed block described above is:
Pellet height=1.27 mm
Pellet cross-sectional area=5.95 mm²

If the thermal cycler was to be used as part of another instrument, e.g. integrated with detection technology, then it may be more convenient to use a different current source which would lead to a modified thermoelectric device geometry. The current source in the present embodiment consists of a class D type switch-mode power amplifier with a current sensing resistor in series with the device and ground.

Because the thermoelectric devices are soldered together, excess solder can wick up die side of the bismuth telluride pellets. Where this occurs, k is increased which results in a local cold spot, also called a mild spot. These cold spots are reduced in number and severity by application of the minimum amount of solder during the assembly process of the thermal electric device. For the same reason, it is also necessary to ensure that the solder used to attach the connecting wires to the thermoelectric device does not contact the pellet High temperature solder has been shown to not only have improved high temperature performance but it is also generally more resistant to failure by stress reversals and hence is most appropriate in this application. The solder used in this invention may be of the type as described in U.S. Pat. No. 5,441,576.

Heatsink

Figure 3:
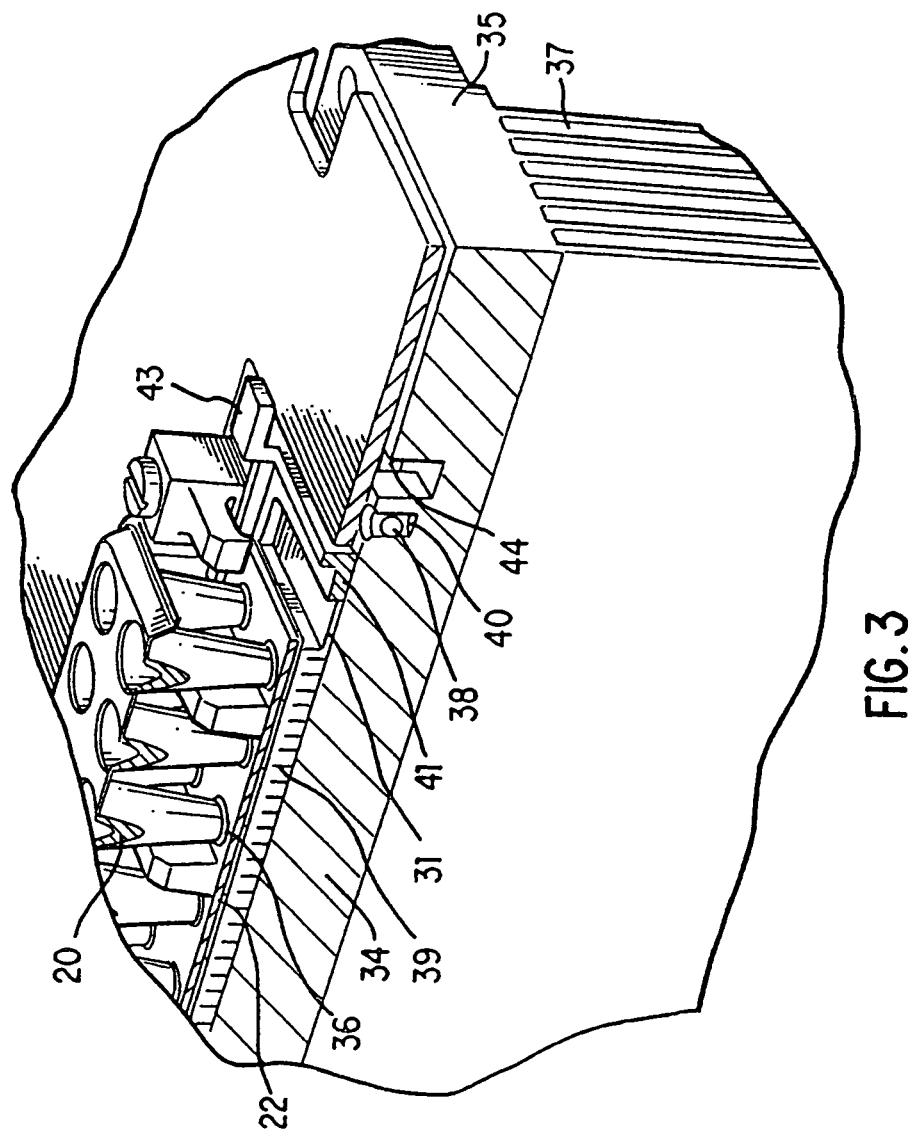
FIG. 3 is a cutaway, partial, isometric view of tie heatsink according to the invention.
Figure 9:
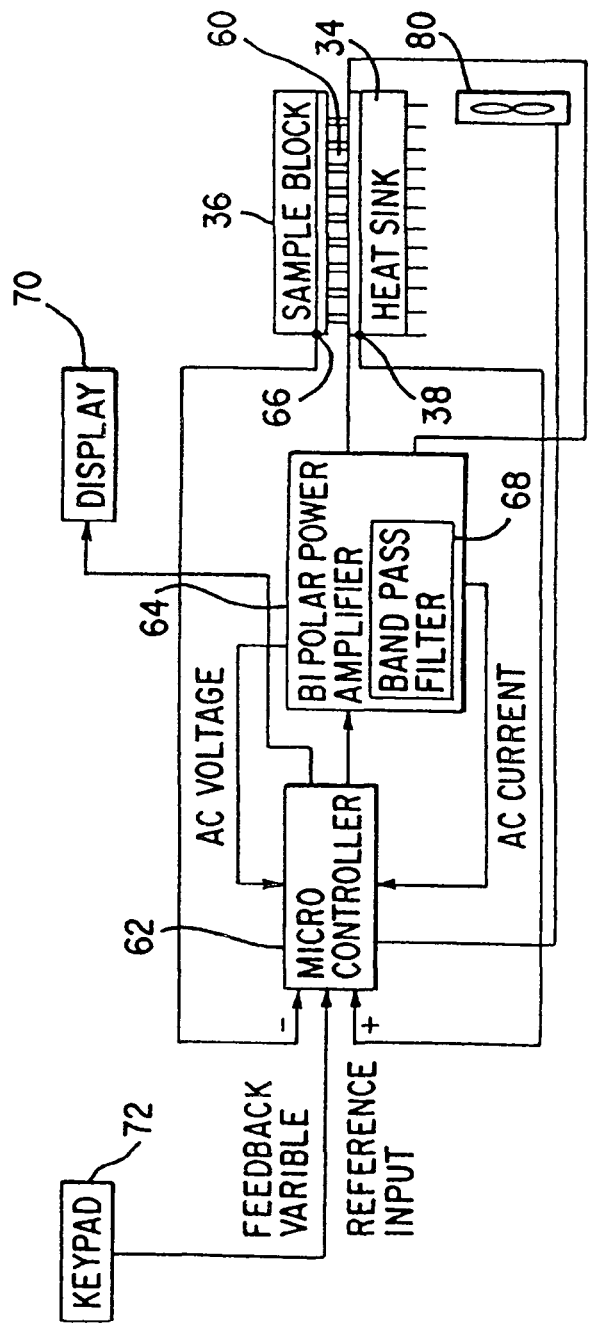
FIG. 9 is a block diagram of the AC resistance measurement circuit of the invention.

FIG. 3 shows the heatsink 34 assembled with the thermoelectric devices 39 and the sample block 36. A locating frame 41 is positioned around the thermoelectric devices to align them with the sample block and the heatsink to ensure temperature uniformity across the sample block. The frame is composed of Ultem or other suitable material and has tabs 43 at its corners to facilitate handling. The heatsink 34 has a generally planer base 34 and fins 37 extending from base 35. The thermal mass of the heat sink is considerably larger than the thermal mass of the sample block and samples combined. The sample block and samples together have a thermal mass of approximately 100 joules/° K and that of the heat sink is approximately 900 joules/° K. This means that the sample block clearly changes temperature much faster than the heat sink for a given amount of heat pumped. In addition the heat sink temperature is controlled with a variable speed fan as shown in FIG. 9. The temperature of the heat sink is measured by a thermistor 38 placed in a recess 40 within the heatsink and the fan speed is varied to hold the heat sink at approximately 45° C. which is well within the normal PCR cycling temperature range, where maintaining a stable heat sink temperature improves the repeatability of system performance. When the block temperature is set to a value below ambient then the heat sink is set to the coolest achievable temperature to reduce system power consumption and optimize block thermal uniformity. This is accomplished simply operating the fan at full speed.

The heat sink temperature measurement is also used by the thermoelectric device control algorithm described below in linearizing the thermal output power from the thermoelectric devices.

The heatsink temperature uniformity is reflected in the uniformity of the block temperature. Typically the heatsink is warmer in the middle than it is at the edges and this adds to other effects that lead to tie corners of the block being the coldest. A trench 44 is cut into the heat sink outside the perimeter of the thermoelectric device area to limit the conduction of heat and decreases edge losses from the area bounded by the trench.

Thermal Interface and Clamping Mechanism

Thermoelectric device manufacturers recommend that thermoelectric devices be held under pressure to improve life-expectancy. (The pressure recommended is often defined by the thermal interface media selected.) The pressure that is recommended varies from manufacturer to manufacturer but is in the range of 30 to 100 psi for cycling applications.

There arc many thermal interface media available in sheet form which can be used to act as a compliant layer on each side of the thermoelectric devices, but it has been demonstrated that thermal grease gives far superior thermal performance for this application. Unlike other compliant sheets which have been shown to require 30 psi or more even under optimal conditions, thermal grease does not require high pressure to ensure that good thermal contact has been made. Also thermal grease acts as an effective lubricant between the expanding and contracting silver block and the thermoelectric device surface, enhancing life-expectancy. Thermalcote II thermal grease manufactured by Thermalloy, Inc. may be used.

Because the silver block is relatively flexible and soft it cannot transmit lateral clamping pressure very effectively. However, because the thermal interface media is thermal grease, the clamping force required is low.

Figure 4:
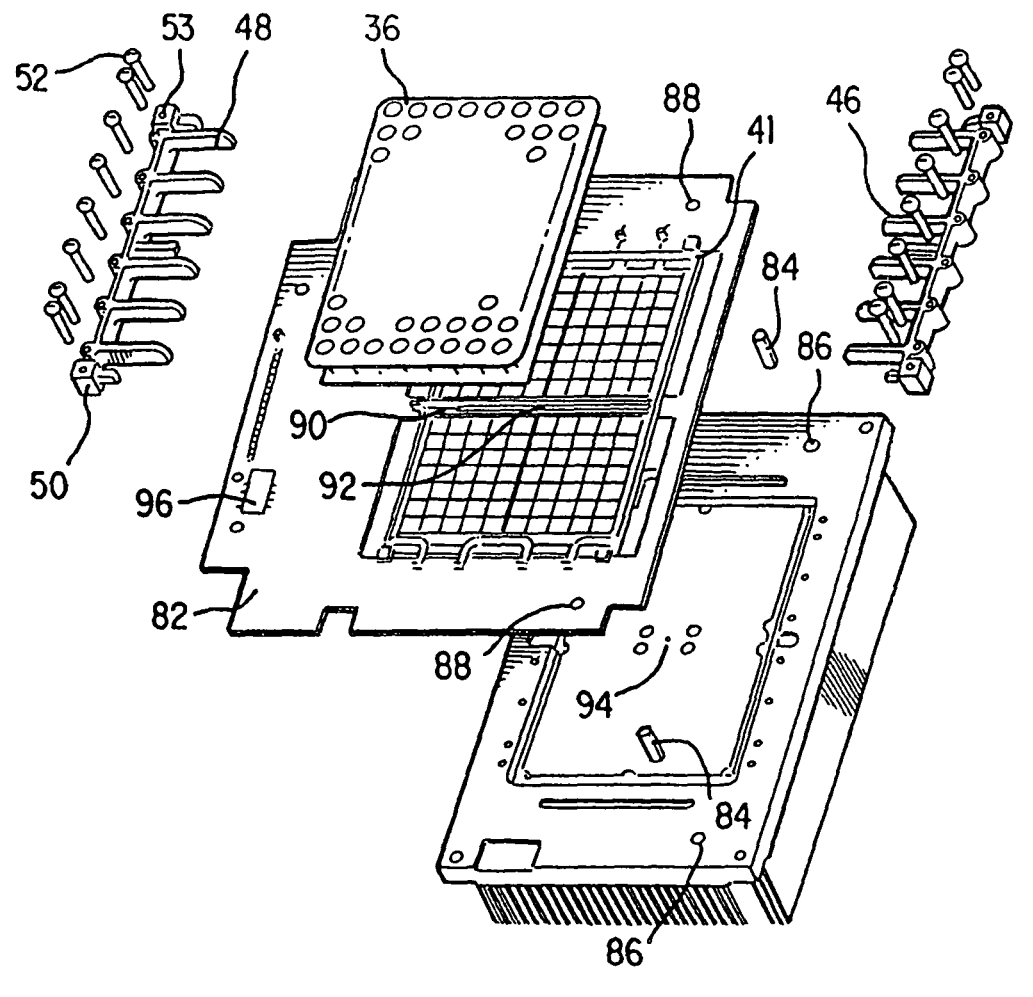
FIG. 4 is an exploded view of an assembly including a sample block, thermoelectric devices and heatsink.

FIG. 4 shows an exploded view of the assembly with the preferred embodiment of the clamping mechanism. Each clamp 46 is made up of a series of fingers 48 extending from a spine 49. The fingers 48 are sized, shaped and spaced so as to fit between the wells 20 of the sample block 36 and thus apply pressure at a corresponding series of points on the base plate 22 of the sample block 36. The open honeycomb structure of the electroformed sample wells allows the fingers to be inserted some distance into the block, thereby applying the pressure more evenly than an edge clamping scheme would. These fingers apply pressure at a series of local points to minimize the contact area between the mass of the clamp and the sample block so that die clamp does not add significantly to the thermal load. The clamps are molded from a glass filled plastic which has the necessary rigidity for this application. The pressure is applied by deforming the fingers with respect to mounting posts 50 which may be separate clamp structures, but arc preferably integrally formed with the clamps 46. The clamps 46 arc held flush to the surface of the heat sink with a series of screws 52 extending through corresponding hole 53 in clamps 46 and then into threaded holes 55 in heatsink 34. This scheme eliminates the necessity to set the pressure with adjustment screws as the clamps can simply be tightened down by standard torqueing techniques.

The resulting even pressure distribution ensures that the full area of the thermo-electric devices is in good thermal contact with the block and the heatsink reducing local thermal stresses on the thermoelectric devices.

FIG. 4 shows other important features of the invention. A printed circuit board 82 includes a memory device 96 for storing data and surrounds the thermoelectric devices and provides electrical connections. Alignment pins 84 are seated in holes 86 in the heatsink and protrude through alignment holes 88 to align the printed circuit board with the heatsink. The locating frame 41 is positioned around the thermoelectric devices and has a cross beam 90 with a through hole 92. Pin 24 (shown in FIG. 1) fits into a hole (not shown) in the sample block, extends through hole 92 in the locating frame and further extends into hole 94 in the heatsink.

Perimeter Heater

Figure 10:
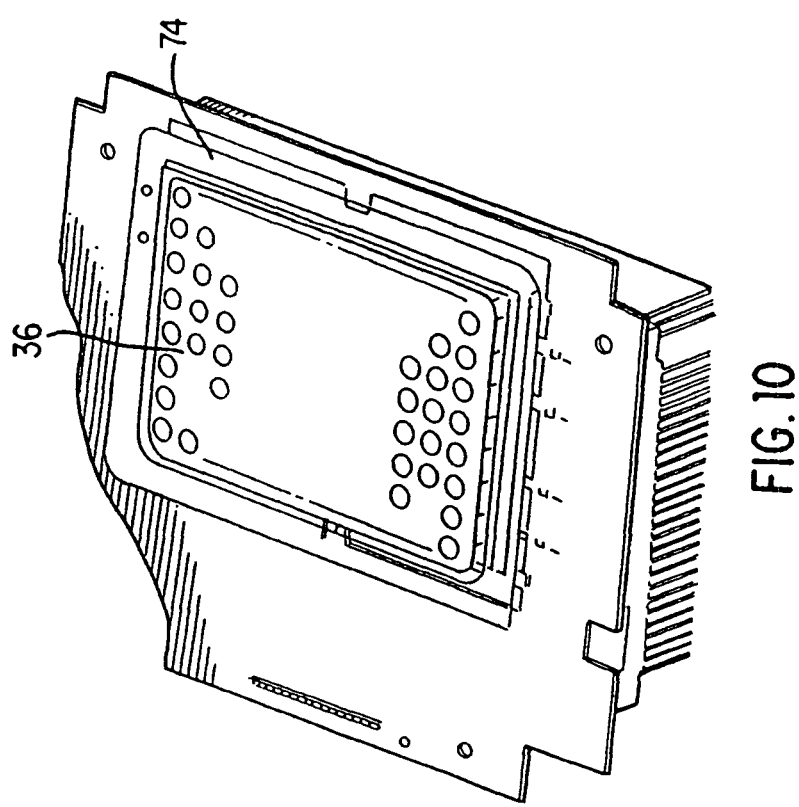
FIG. 10 shows a perimeter heater and its location surrounding the sample block.

In order to bring the temperature uniformity across the sample block to approximately ±0.2° C., a perimeter heater is positioned around the sample block to eliminate heat losses from its edges. Preferably, the heater is a film type, having low mass with inside dimensions slightly larger than the sample block. FIG. 10 shows the perimeter heater 74 and its approximate location surrounding the sample block 36. The heater is not fastened in place, it is simply positioned in the air around the perimeter of the sample block in order to warm the air in the immediate vicinity.

Figure 11:
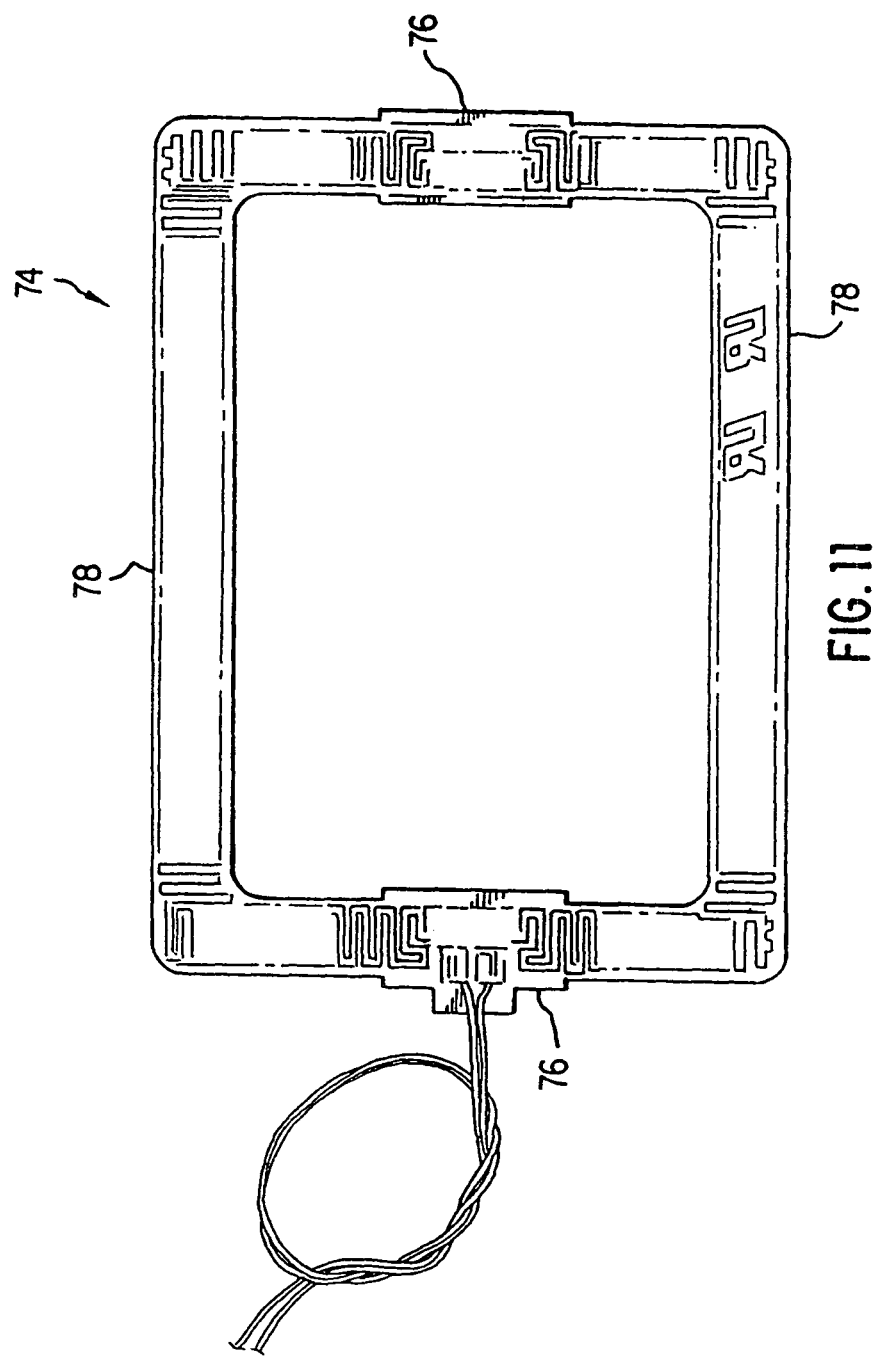
FIG. 11 is a detailed view of the perimeter heater of FIG. 10.

FIG. 11 shows a detailed view of the perimeter heater 74. The heater is rectangular as determined by the dimensions of the sample block and is manufactured so that it has separate power densities in specific areas to reflect the varying amounts of heat loss around the perimeter of the block. Matching lower power density regions 76 (0.73 W/in$^2$) are located in the center portions of the short sides of the rectangle and matching higher power density regions 78 (1.3 W/in$^2$) are located in the longer sides, extending into the shorter sides.

Figure 12:
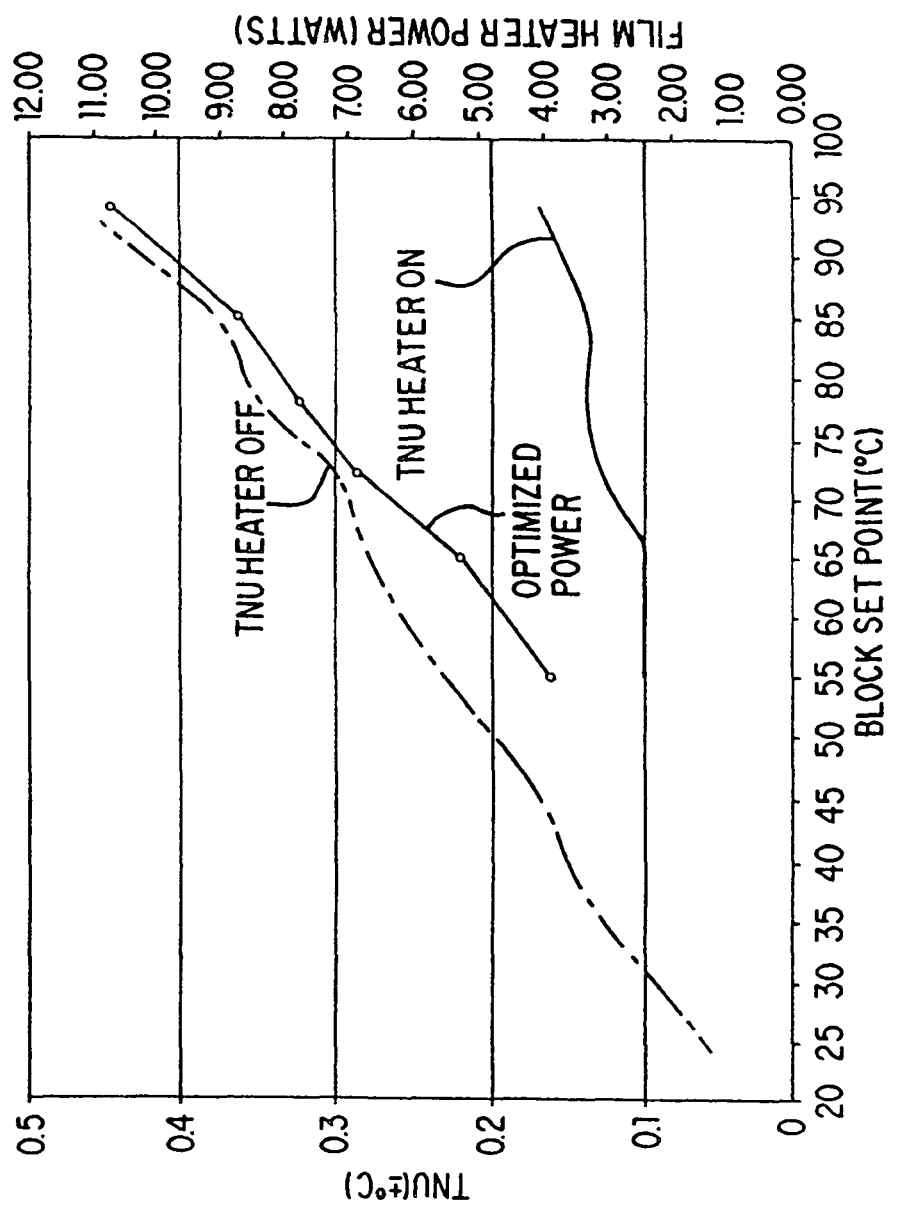
FIG. 12 shows the power applied to the perimeter heater as a function of the temperature of the sample block.

As shown in FIG. 12, the power applied to the perimeter heater is regulated to correspond to the temperature of the sample block with more power applied to the heater at higher block temperatures and less applied at lower block temperatures.

Figure 5:
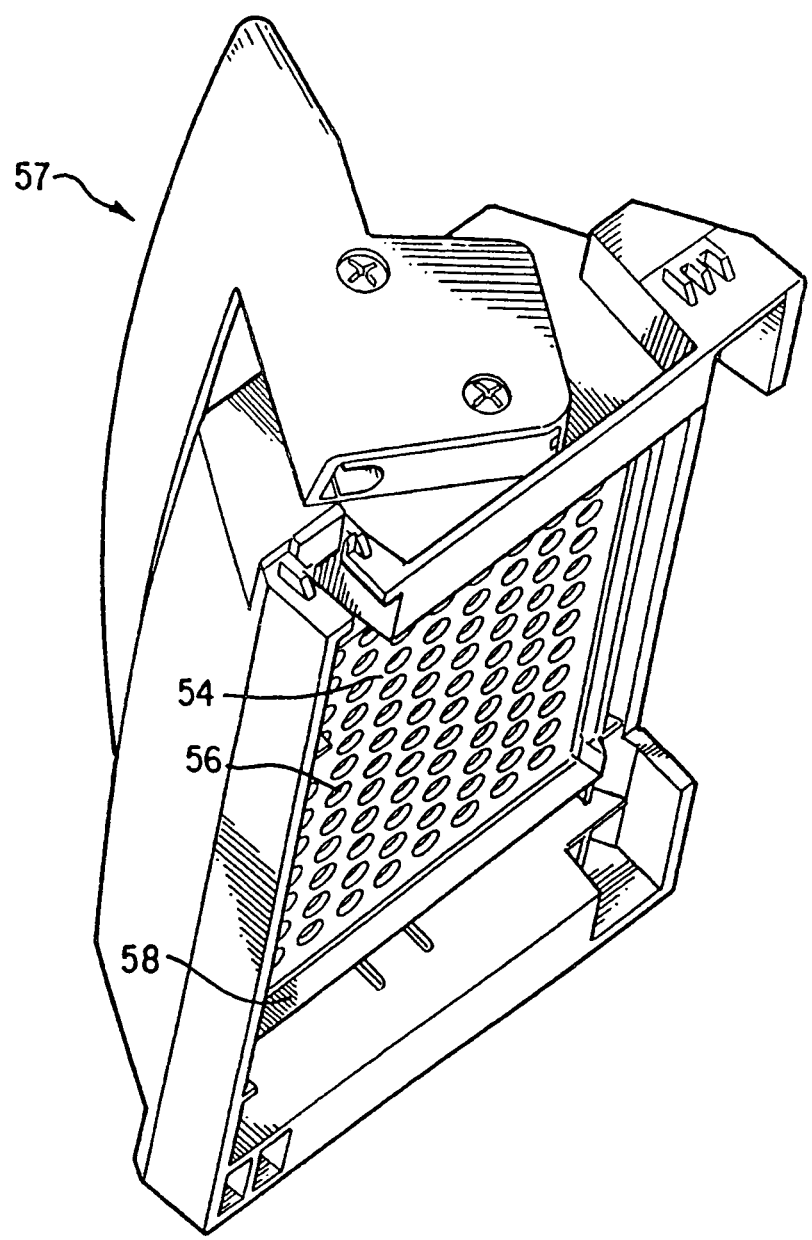
FIG. 5 is an isometric view of the heated cover in accordance with the invention

Heated Cover:

FIG. 5 shows the heated cover 57. The heated cover applies pressure to the sample vial caps to ensure that they remain tightly closed when the sample is heated.

Further, pressure transferred to the vials assures good thermal contact with the sample block. The cover is heated under computer control to a temperature above that of the sample to ensure that the liquid does not condense onto the tube cap and instead remains in the bottom of the tube where thermal cycling occurs. This is described in U.S. Pat. No. 5,475,610, mentioned above. The heated platen 54 in the present invention does not press on the dome of the cap but instead presses on the cap perimeter. The platen has a surface shaped in this manner so that optical caps are not distorted by the application of pressure. Thus, tubes that have been cycled can be directly transferred to an optical reader without the need to change the cap.

Because the heated platen has recesses 56 in it to clear the cap domes, there is a need to align the plate to die tube positions before applying pressure to avoid damage to the tubes. This is accomplished by use of a "skirt" 58 around the perimeter of the platen which aligns to the microtiter tray before the plate touches the tube caps. The cover has a sliding mechanism similar to that used on the PYRIS Differential Scanning Calorimeter by the Perkin Elmer Corporation allowing the cover to slide back to allow sample vials to be inserted into the sample block and forward to cover the sample block and move down engage the vials.

Determining the Ideal Ramp Rate:

The optimized ramp rate has been empirically determined to be 4° C./sec. Any system which has a higher block ramp rate than this cannot fully utilize the benefits of temperature overshoots and consequently achieves an insignificant reduction in cycle time.

Figure 6:
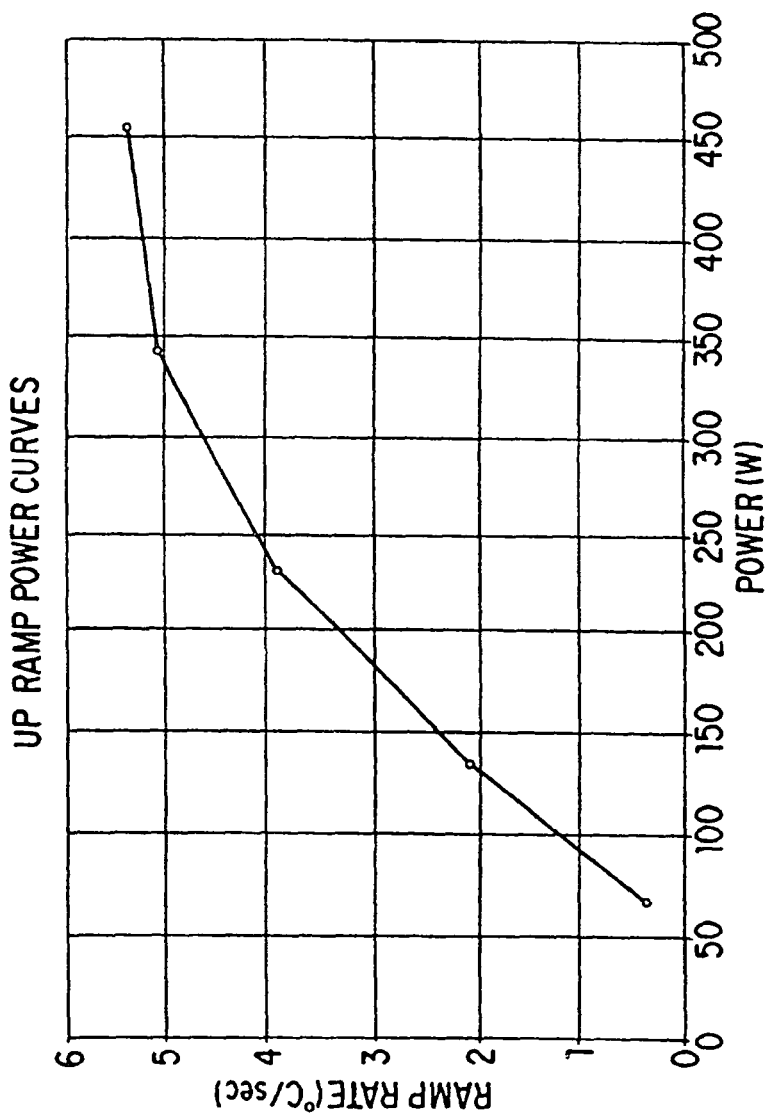
FIG. 6 is a chart depicting the Up Ramp (heating rate) vs. Power.
Figure 7:
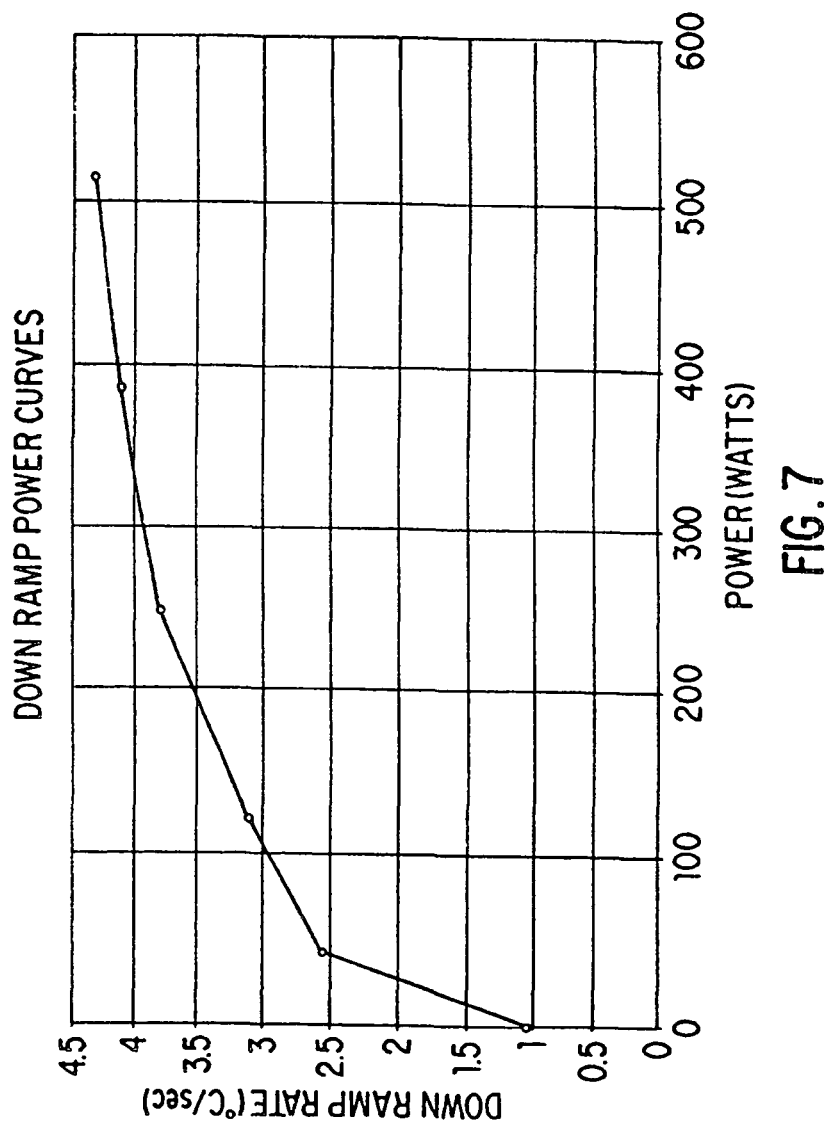
FIG. 7 is a chart depicting the Down Ramp (cooling rate) vs. Power.

FIG. 6 is a chart depicting the Up Ramp (heating rate) vs. Power and FIG. 7 is a chart depicting the Down Ramp (cooling rate) vs. Power.

When heating the block to a temperature above ambient, the Joule heating and the Seebeck heat pumping both act to heat the sample block against conduction. When cooling the block between two temperatures above ambient, the Seebeck heat pumping and conduction act against the Joule heating. During cooling, significant power is required to hold the block temperature steady against the flow of heat out of the block by conduction. Therefore even with zero power applied, the block will cool at a significant rate. As the current is increased, the Seebeck effect increases the cooling obtained. However as the current is increased further the joule effect, which is proportional to the square of the current, quickly starts to take over acting against the Seebeck cooling. Therefore a point is reached where applying additional power acts against die required effect of cooling. In the heating mode these two effects act together against conduction and no ceiling is reached. In practice the heating power vs. input current is approximately linear. This is why the design criteria centers around meeting the cooling rate requirements; the heating rate can always be achieved by the application of more power.

Characterizing the Output of the TED's

The following equation describes the total heat flow from the cold side of a thermal electric cooler.

$$0 = 1/2 * R(t_{avg}) * I^2 + t_c * S(t_{avg}) * I - (k(t_{avg}) * (t_c - t_h) + Q_c)$$

where $T_c$ = cold side temperature of cooler
$t_h$ = hot side temperature of cooler
$t_{avg}$ = average of $t_c$ and $t_h$
R(t) = electrical resistance of cooler as a function of temperature
S(t) = Seebeck coefficient of the cooler as a function of temperature
K(t) = Conductance of cooler as function of temperature
I = electrical current applied to cooler
$Q_c$ = total heat flow from die cold side of the cooler Given a desired heat flow, $Q_c$, and the hot and cold side temperatures, $t_c$ and $t_h$, the equation is solved for I, the current required to produce $Q_c$. The solution of this equation is used for three purposes:

1) To achieve linear temperature transitions or ramps.

For linear temperature transitions, constant thermal power is required. To maintain constant thermal power when temperatures $t_c$ and $t_h$ are changing, it is necessary to solve for I in equation 1 periodically. The result is the current then applied to the coolers. To compensate for errors a proportional integral derivative (PID) control loop is applied where:

Error input to *PID* = Set point Rate − Actual Rate and Output from the PID is interpreted as percent Q 2) To achieve a linear PID temperature set point control algorithm over the desired temperature range:

Input to the PID control is the error signal $t_c$−Set point.
Output from the PID control is interpreted as a % of $Q_{max}$.
Equation 1 is used to determine the current value, I, which will result in the % of $Q_{max}$ output by the PID control, under the current temperature conditions.

3) To achieve non-linear temperature transitions or ramps where temperature transitions are defined by the derivative of temperature with respect to time, dT/dt, as a function of block temperature.

This function is approximated by a table containing Block temperature T, dT/dt data points in 5 C increments for cooling and by a linear equation for heating. The small effect of sample mass on dT/dt profiles, although measurable, is ignored. Knowing the total thermal mass, $MC_p$(joules/° K), involved during temperature transitions, the amount of thermal power, Q (Joules/sec), required to achieve the desired rate profile, dT/dt (° K/sec), is given at any temperature by the following equation:

$$Q = MC_p * dT/dt$$

The solution to equation 1 is used to determine the current value, I, which will result in the desired Q under the current temperature conditions. This process is repeated periodically during temperature transitions.

Controlling Overshoot and Undershoot

There is a practical limit to the ramp rates and the resulting cycle times that can be achieved. The sample has a time constant with respect to the block temperature that is a function of the sample tube and tube geometry which, because the tube is an industry standard, cannot be reduced. This means that even if the sample tube wall temperature is changed as a step function e.g. by immersion in a water bath, the sample will have a finite ramp time as the sample temperature exponentially approaches the set point. This can be compensated for by dynamically causing the block to overshoot the programmed temperature in a controlled manner. This means that the block temperature is driven beyond the set point and back again as a means of minimizing the time taken for the sample to reach the set point. As the possible ramp-rates increase, the overshoot required to minimize the time for the sample to reach the set point gets larger and a practical limit is soon reached. This occurs because although the average sample temperature does not overshoot the set point, the boundary liquid layer in the tube does overshoot to some extent. When cooling to the priming temperature, too great an overshoot can result in non-specific priming. Therefore the best advantage is to be gained in a system which utilizes this maximum ramp rate combined with optimized overshoots that are symmetrical on both up and down ramps.

Figure 8:
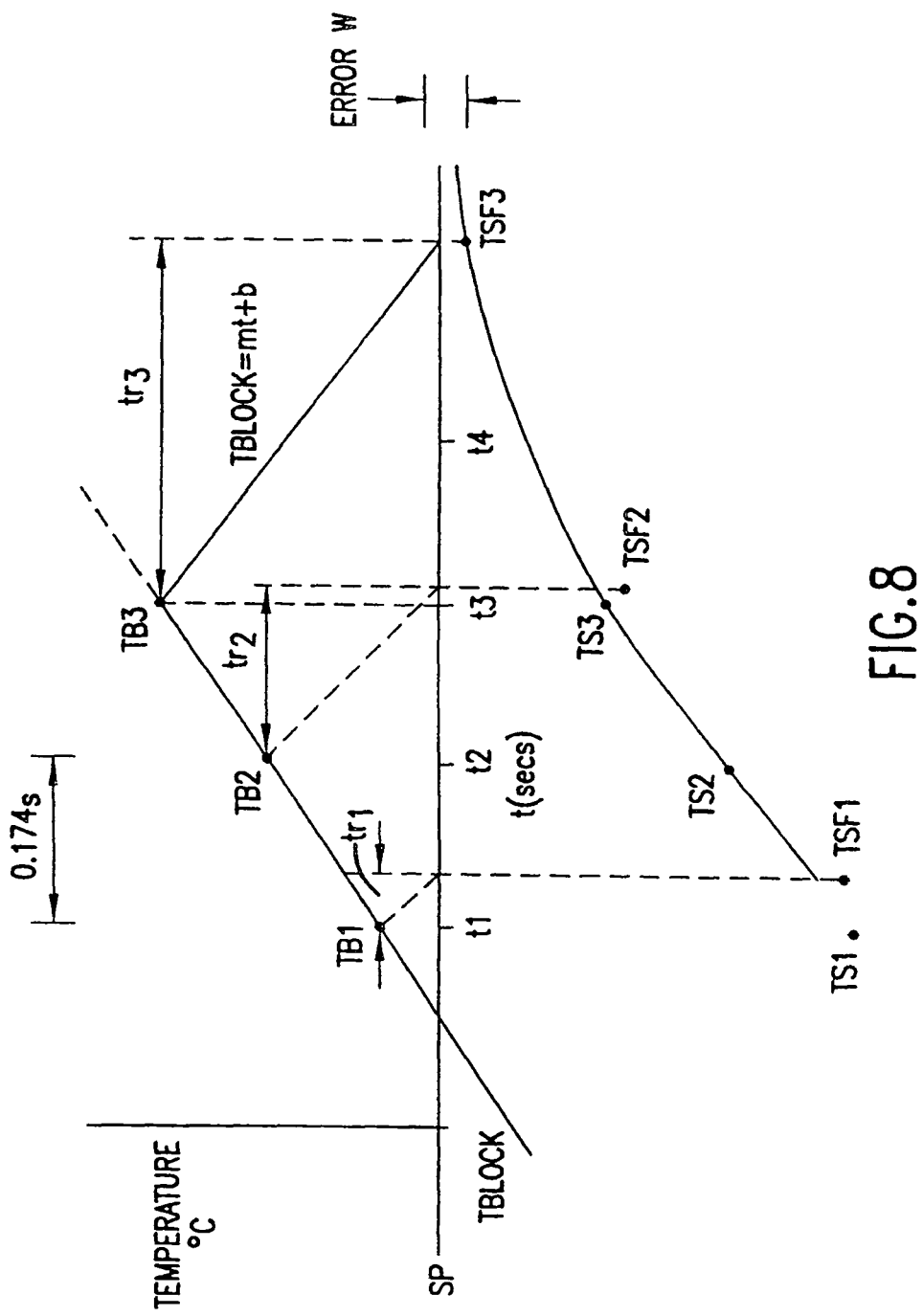
FIG. 8 is a chart for predicting and compensating for temperature overshoots and undershoots in accordance with the invention.

FIG. 8 is a chart for predicting and compensating for temperature overshoots and undershoots. In order to drive the block temperature beyond the set point and back again in a controlled fashion the system first measures the block temperature, $Tb_{n+1}$ and then solves the following equations:

$$Ts_{n+1} = Ts_n + (Tb_{n+1} - Ts_n) * 0.174/RC$$

$$Tsf_n = (Tb_n - Ts_n - mRC)(1 - e^{-tm/RC}) + mtr_n + Ts_n$$

where Tb is the measured block temperature, Ts is the calculated sample temperature, Tsf is the final calculated sample temperature if the block is ramped down at time $t_n$, R is the thermal resistance between the sample block and the sample, C is the thermal capacitance of the sample, m is the slope of a line defined by the points Tb and Tsf and tr is the time for the sample block to return to the set point if the system caused it to ramp toward the set point at the same rate it is was ramping away.

If the resulting $Tsf_n$ is within a particular error window around the set point then the system causes the sample block to ramp back to the set point at the same rate it was ramping away. If the resulting $Tsf_n$ is outside the particular error window then the system causes the sample block to continue to ramp away from the set point at the same rate. While ramping back toward the set point the same proportional integral derivative (PID) control loop described above is applied.

Determining Sample Temperature

Figure 13:
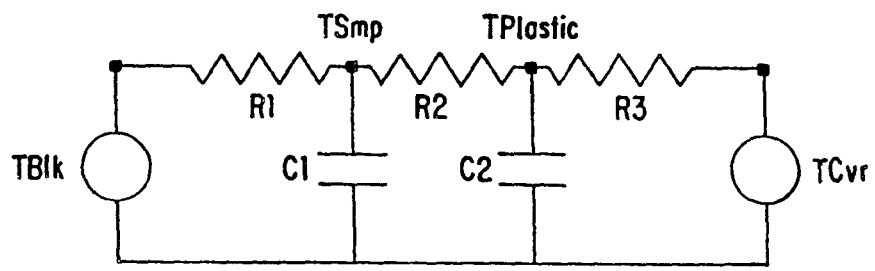
FIG. 13 shows a thermal model of a sample in a sample vial.

The temperature of a sample in a sample vial is determined by using the model illustrated in FIG. 13 where:
TBlk is the measured baseplate temperature;
TSmp is the calculated sample temperature;
TPlastic is the calculated plastic temperature;
TCvr is the measured cover temperature;
R1 is the thermal resistance of the plastic vial between the block and sample mixture;
C1 is the thermal capacitance of the sample mixture;
R2 and R3 represent the thermal resistance of air in parallel with the plastic vial between the sample mixture and the cover; and
C2 is the thermal capacitance of the plastic vial between the sample mixture and the cover.

Figure 14:
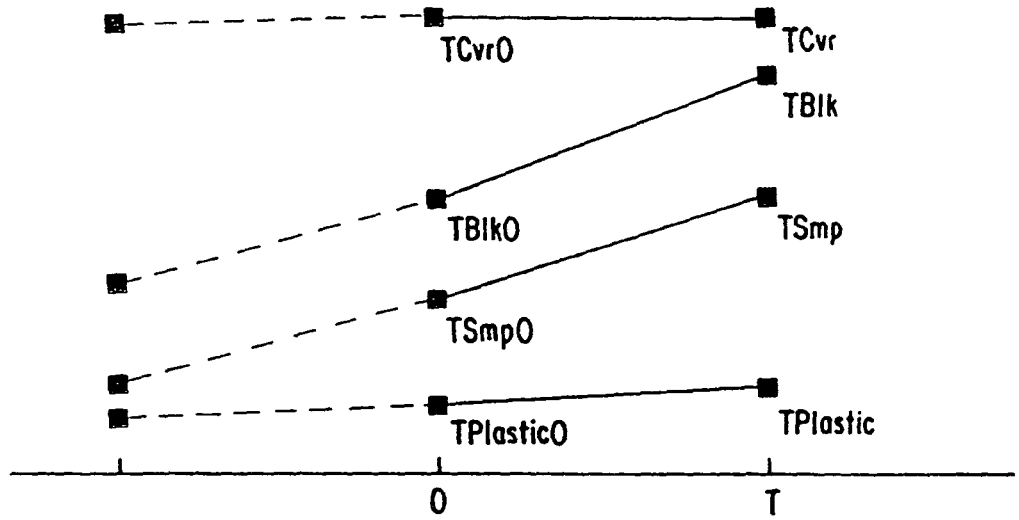
FIG. 14 is an illustration of the initial conditions of the thermal model of FIG. 13.

The model above is solved for TSmp(t) and TPlastic(t) given that: TBlk=mt+ TBlk0, TCvr=K and initial conditions are non-zero. Taking initial conditions and the slope of TBlk to be the only variables, as illustrated in FIG. 14, the equations are refactored giving equations for Tsmp and TPlastic.

Given the following relationships:

$$g1 = 1/R1;$$

$$g2 = 1/R2;$$

$$g3 = 1/R3;$$

$$a = (g1+g2)/C1;$$

$$b = g2/C1;$$

$$f = g2/C2;$$

$$g = (g2+g3)/C2;$$

$$alpha = -(-g/2 - a/2 - (\sqrt{g*g - 2*g*a + a*a + 4*f*b}))/2);$$
and $$beta = -(-g/2 - a/2 + (\sqrt{g*g - 2*g*a + a*a + 4*f*b}))/2),$$

the coefficients for the sample temperature equation become:

$$coef1 = (g3/C2)*(-b/(beta*(alpha-beta))*exp(-bta*T) + b/(alpha*beta) + (b/(alpha*(alpha-beta)))*exp(-alpha*T))$$

$$coef2 = (b/(alpha-beta))*exp(-beta*T) - (b/(alpha-beta))*exp(-alpha*T)$$

$$coef3 = (g1/C1)*(g/(alpha*beta) + (-alpha+g)*exp(-alpha*T)/(alpha*(alpha-beta)) + (beta-g)*exp(-beta*T/(beta*(alpha-beta))))$$

$$coef4 = (g1/C1)*((g-beta)*exp(-beta*T)/(pow(beta,2)*(alpha-beta)) - g/(beta*pow(alpha,2)) + (1+T*g)/(alpha*beta) + (-g+alpha)*exp(-alpha*T)/(pow(alpha,2)*(alpha-beta)) - g/(alpha*pow(beta,2)))$$

$$coef5 = (-g+alpha)*exp(-alpha*T)/(alpha-beta) + (g-beta)*exp(-beta*T)/(alpha-beta)$$

and the coefficients for the plastic vial temperature equation become:

$$coef6 = (g3/C2)*((beta-a)*exp(-beta*T)/(beta*(alpha-beta)) + a/(alpha*beta) + (-alpha+a)*exp(-alpha*T)/(alpha*(alpha-beta)))$$

$$coef7 = (-beta+a)*exp(-beta*T)/(alpha-beta) + (alpha-a)*exp(-alpha*T)/(alpha-beta)$$

$$coef8 = (g1/C1)*(f*exp(-beta*T/(pow(beta,2)*(alpha-beta)) - f/(beta*pow(alpha,2)) - f*exp(-alpha*T)/(pow(alpha,2)*(alpha-beta)) + T*f/(alpha*beta) - f/(alpha*pow(beta,2)))$$

$$coef9=(g1/C1)*(-f*\exp(-beta*T)/(beta*(alpha-beta))+f/(alpha*beta)+f*\exp(-alpha*T)/(alpha*(alpha-beta)))$$

$$coef10=f*\exp(-beta*T)/(alpha-beta)-f*\exp(-alpha*T)/(alpha-beta)$$

and $$slope=(TBlk-TBlk0)/T \text{ where } T \text{ is the sampling period (0.174 sec)}$$

Utilizing the model in FIG. 13 then, $$TSmp=coef1*TCvr0+coef2*TPlastic0+coef3*TBlk0+coef4*slope+coef5*TSmp0$$

$$TPlastic=coef6*TCvr0+coef7*TPlastic0+coef8*slope+coef9*TBlk0+coef10*TSmp0$$

The coefficients are recalculated at the beginning of each PCR protocol to account for the currently selected sample volume. TSmp and TPlastic are recalculated for every iteration of the control task.

To determine the sample block set point, TBlkSP, during a constant temperature cycle, Tblk is determined using the equation for TSmp.

$$Tblk0(Tsmp-coef1*TCvr0-coef2*TPlastic0-coef4*slope-coef5*TSmp0)/coef3$$

When maintaining a constant temperature the slope=0 and Tsmp=Tsmp0=TSmpSP (sample temperature set point) and:

$$TBlkSP=(TSmpSP-coef1*TCvr-coef2*TPlastic-coef5*TSmpSP)/coef3$$

The equation for TBlkSP is solved on every pass of the control loop to update the sample block set point to account for changes in temperature of the plastic and cover.

Calibration Diagnostics:

The control software includes calibration diagnostics which permit variation in the performance of thermoelectric coolers from instrument to instrument to be compensated for so that all instruments perform identically. The sample block, thermoelectric devices and heatsink are assembled together and clamped using the clamping mechanism described above. The assembly is then ramped through a series of known temperature profiles during which its actual performance is compared to the specified performance. Adjustments are made to the power supplied to the thermoelectric c devices and the process is repeated until actual performance matches the specification. The thermal characteristics obtained during this characterization process arc then stored in a memory device residing on the assembly. This allows the block assembly to be moved from instrument to instrument and still perform within specifications.

AC Resistance Measurement:

The typical failure mode for the thermoelectric devices is an increase in resistance caused by a fatigue failure in a solder joint. This results in an increase in the temperature of that joint which stresses tie joint further, rapidly leading to catastrophic failure. It has been determined empirically that devices that exhibit an increase in AC resistance of approximately 5% after about 20,000 to 50,000 temperature cycles will shortly fail. The AC resistance of the thermoelectric devices are monitored by the instrument to detect imminent failures before the device in question causes a thermal uniformity problem.

This embodiment automates the actual measurement using a feedback control system and eliminates the need to remove the thermoelectric device from the unit. The control system compensates for the temperature difference between the two surfaces of the thermoelectric device caused by the heat sink attached to one side and the sample block attached to the other. The control system causes the thermoelectric device to equalize its two surface temperatures and then the AC resistance measurement is made. The micro-controller performs a polynomial calculation at the referenced time of the AC measurement to compensate for ambient temperature error.

FIG. 9 shows the sample block 36, a layer of thermoelectric device 60 and heatsink 34 interfaced with the system micro-controller 62 and bipolar power amplifier 64. The temperature sensor is already present in the heatsink 38 and an additional temperature sensor attached to the sample block 36 with a clip (not shown) formed of music wire are utilized to determine the temperature differential of the surfaces of the thermoelectric device.

The bipolar power amplifier supplies current in two directions to the device. Current in one direction heats the sample block and current in the other direction cools the sample block. The bipolar power amplifier also has signal conditioning capability to measure the AC voltage and AC current supplied to the thermoelectric device. A band pass filter 68 is incorporated into the signal conditioning to separate an AC measurement signal from the steady state signal that produces a null condition for the temperature difference across the thermoelectric device.

The micro-controller incorporates the necessary capability to process the measurement information and perform the feedback in real time. It also stores the time history of the AC resistance and the number of temperature cycles of the thermoelectric device and displays the information to die operator on the display 70. Tie AC measurement is normally done during initial turn on. However, it can be activated when self diagnostics are invoked by the operator using the keypad 72. An analog to digital and digital to analog converter along with signal conditioning for the temperature sensors and AC resistance measurement is also integrated into the micro-controller in order for it to perform its digital signal processing.

Sealing the Thermoelectric Device Area from the Environment.

Figure 15:
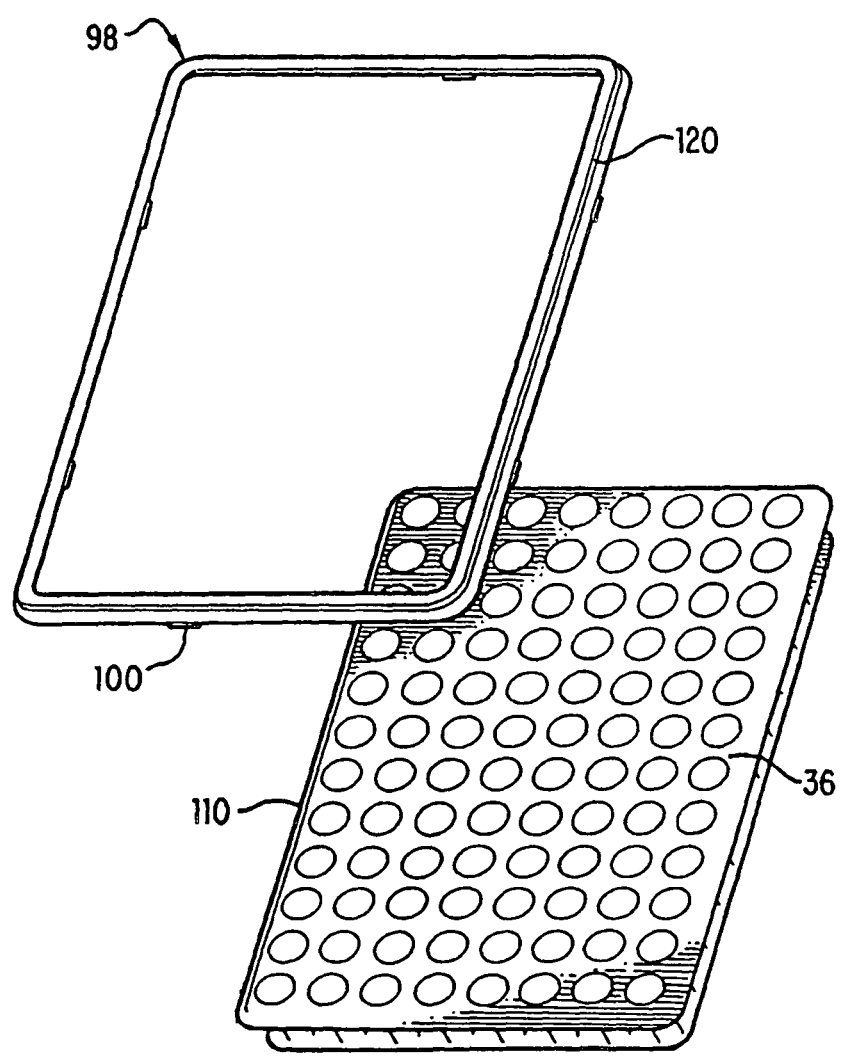
FIG. 15 shows the sample block and a seal designed to protect the thermoelectric devices from the environment.

The thermoelectric devices are protected from moisture in the environment by seals and the chamber is kept dry with the use of a drying agent such is silica gel. The seal connects from the silver electroform to the surrounding support and as such adds to the edge losses from the block. These losses arc minimized by the use of a low thermal conductivity pressure seal 98 and by the use of the perimeter heater described above. The seal 98 has a cross-section generally in the shape of a parallelogram with several tabs 100 spaced about the lower surface of seal 98 for holding seal 98 to the edge of the sample block as shown in FIG. 15.

The seal 98 is installed by first applying RTV rubber (not shown) around the perimeter 110 of the upper portion of the sample block The seal 98 is then placed on the RTV rubber. More RTV rubber is applied to the perimeter 120 of the seal and then a cover (not shown) is installed which contacts the RTV rubber-seal combination. The cover has a skirt which also contacts a gasket (not shown) on the printed circuit board to effect a more effective seal.

What is claimed:
1. A system comprising:
   a first instrument comprising:
      an assembly for cycling a plurality of vials through a series of temperatures;
      a heated cover;
      wherein the assembly comprises
         a sample block configured to receive a plurality of vials;
         a printed circuit board;

at least one Peltier thermoelectric device configured to heat and cool the sample block, the at least one Peltier thermoelectric device surrounded by the printed circuit board, wherein the printed circuit board is positioned to align the at least one Peltier thermoelectric device with the sample block and a memory device in electrical communication with the first instrument; and a second instrument, wherein the assembly is configured to be removable from the first instrument and attachable to the second instrument for cycling a plurality of vials through a series of temperatures.

2. The system of claim 1, further comprising a plurality of vials received in the sample block.

3. The system of claim 2, wherein the cover is configured to apply a seating force to the plurality of vials.

4. The system of claim 2, wherein the plurality of vials comprises a microtiter tray.

5. The system of claim 2, wherein the plurality of vials further comprise a liquid reaction mixture disposed therein.

6. The system of claim 5, wherein the liquid reaction mixture comprises polymerase chain reaction reagents.

7. The system of claim 1, wherein the sample block comprises a plurality of sample wells configured to receive the plurality of vials.

8. The system of claim 7, wherein the sample block comprises 96 sample wells.

9. The system of claim 7, wherein the sample wells are arranged in an 8×12 array.

10. The system of claim 7, wherein the sample block comprises silver.

11. The system of claim 7, wherein the sample block has a rectangular top surface.

12. The system of claim 7, wherein the sample block comprises an upper support plate configured to connect to the tops of the sample wells and a bottom plate configured to connect to the bottoms of the sample wells.

13. The system of claim 12, wherein the upper support plate and the sample wells are electroformed as a single piece.

14. The system of claim 12, wherein the sample block has a thermal mass and the bottom plate comprises the bulk of the thermal mass of the sample block.

15. The system of claim 1, wherein the Peltier thermoelectric device comprises a plurality of Peltier thermoelectric devices.

16. The system of claim 15, wherein the plurality of Peltier thermoelectric devices are matched to within 0.2° C.

17. The system of claim 1, further comprising a computing apparatus configured to control the temperature of the cover.

18. The system of claim 1, wherein the assembly further comprises a heat sink and the Peltier thermoelectric device is positioned between the sample and the heat sink.

19. The system of claim 18, further comprising a clamping mechanism positioned to clamp the Peltier thermoelectric device between the sample block and the heat sink.

20. The system of claim 1, further comprising a computing apparatus for controlling the temperature of the assembly, and wherein the Peltier thermoelectric device is controlled by the computing apparatus.

21. An apparatus comprising:
an assembly for cycling a plurality of vials through a series of temperatures; and
wherein the assembly comprises
a memory device,
a heat sink,
a sample block configured to receive a plurality of vials,
at least one Peltier thermoelectric device configured to heat and cool the sample block, and
a locating frame positioned around the at least one Peltier thermoelectric device to align the at least one Peltier thermoelectric device with the heat sink;
wherein the assembly is configured to be removable from the apparatus and attached to a different apparatus for cycling a plurality of vials through a series of temperatures and wherein the memory device is configured to enable performance of the assembly on the different apparatus.

22. The system of claim 1, wherein the heated cover further comprises a plurality of recesses sized to mirror cap dimensions on the plurality of vials.

23. The apparatus of claim 21, wherein the heated cover further comprises a plurality of recesses sized to mirror cap dimensions on the plurality of vials.

24. A system comprising:
a first instrument comprising:
an assembly for cycling a plurality of vials through a series of temperatures;
a heated cover;
wherein the assembly comprises
a sample block configured to receive a plurality of vials;
at least one Peltier thermoelectric device configured to heat and cool the sample block and
a memory device in electrical communication with the first instrument; and
a second instrument,
wherein the assembly is configured to be removable from the first instrument and attachable to the second instrument for cycling a plurality of vials through a series of temperatures.

* * * * *